United States Patent [19]

Berger et al.

[11] 4,233,202
[45] Nov. 11, 1980

[54] PROCESS FOR THE PURIFICATION OF EPOXY COMPOUNDS

[75] Inventors: Dieter Berger; Wilfried Bartz; Wolfgang Seeliger, all of Marl, Fed. Rep. of Germany

[73] Assignee: Chemische Werke Huels Aktiengesellschaft, Marl, Fed. Rep. of Germany

[21] Appl. No.: 765,722

[22] Filed: Feb. 4, 1977

Related U.S. Application Data

[63] Continuation-in-part of Ser. No. 563,163, Mar. 28, 1975, abandoned.

[30] Foreign Application Priority Data

Apr. 3, 1974 [DE] Fed. Rep. of Germany ....... 2416227

[51] Int. Cl.$^3$ .......................................... C07D 301/32
[52] U.S. Cl. ............................................... 260/348.36
[58] Field of Search ....................... 260/348 R, 348.36

[56] References Cited

FOREIGN PATENT DOCUMENTS 119415 8/1966 Czechoslovakia .

Primary Examiner—Norma S. Milestone
Attorney, Agent, or Firm—Millen & White

[57] ABSTRACT

The low molecular water-soluble onium-catalyst dissolved in the liquid mixture of epoxy resin and excess epihalohydrin obtained by the reaction in the presence of base of a compound having —OH, —SH, —COOH or =NH groups with excess 1-halo-2,3-epoxyalkane, is separated therefrom by contacting the liquid mixture, either prior to or after separation therefrom of the precipitated salt produced by the reaction, with at least about 5 parts by weight based on the weight of the catalyst present in the liquid mixture, of an adsorbent containing or capable of absorbing at least 1% by weight of water so strongly that it cannot be removed either by drying over concentrated sulfuric acid or by drying at 110° C. and can only be partially removed by drying at 200° C. under vacuum (about 1 millibar), and then separating the adsorbent with catalyst adsorbed thereon from the liquid mixture.

10 Claims, No Drawings

PROCESS FOR THE PURIFICATION OF EPOXY COMPOUNDS

CROSS-REFERENCE TO OTHER APPLICATIONS

This is a continuation-in-part of application Ser. No. 563,163, filed Mar. 28, 1975 now abandoned.

BACKGROUND OF THE INVENTION

This invention relates to a process for the purification of epoxy resins.

Epoxy compounds or "epoxy resins" are employed primarily as binders in paints and varnishes, as cast resins for the production of laminates, as insulating materials for electric conductors, and as adhesives and thus are of great commercial significance.

These compounds are obtained almost exclusively by glycidylation, i.e., by reacting di- or higher-functional compounds, such as, for example, polyalcohols, polyphenols, polymercaptans, polycarboxylic acids, or amines with, in most cases, excess epihalohydrin (or $\beta$-methylhalohydrin), employing agents which split off hydrogen halide, such as, e.g., alkali metal hydroxide. Generally, epichlorohydrin is employed as the epihalohydrin and the excess epihalohydrin as the reaction solvent.

The functional groups —OH, —SH, —COOH, =NH of these compounds which are reacted with epichlorohydrin can be present not only on a low-molecular residue, such as, for example, arylene or alkylene, but also on a high-molecular organic residue, such as, for example, a polyester or polyurethane chain.

To conduct such glycidylations, for example, as described in German Unexamined Laid-Open Applications DOS No. 1,643,777 and DOS No. 1,816,096, and as generally utilized except in the glycidylation of several polyalcohols, catalysts are employed, viz., tertiary sulfonium, quaternary ammonium, and phosphonium compounds and/or compounds which are converted into these substances under the reaction conditions, e.g., secondary sulfides, tertiary amines, and tertiary phosphines. Such catalysts are known, for example, from the German Patents or Laid-Open Applications Nos. 1,211,177, 1,816,096 and 1,911,478.

By azeotropic distillation with the excess epihalohydrin employed as reaction solvent, the largest portion of the water produced during the reaction is removed from the reaction mixture and the moist (about 3% water content) epihalohydrin is recycled into the reaction mixture.

The reaction yields a mixture consisting essentially of a salt suspension in a solution of the epoxy compound and the catalyst in the excess moist epihalohydrin, the salt being produced during the formation of the glycidyl groups by reaction of the agent splitting off hydrogen halide from the intermediately produced halohydrin. In general, this salt is an alkali halogenide, in most cases, sodium chloride.

To produce the desired epoxy product in pure form, the precipitated salt, the catalyst, and the excess moist epihalohydrin must be removed from this reaction mixture.

The salt can be removed by simple filtration but the catalyst, which is dissolved in the reaction mixture, cannot. Accordingly, in the conventional work-up, after separating the alkali halogenide by filtration or centrifugation, the catalyst is extracted from the mixture with water before the epoxy resin can be isolated by concentrating the resulting solution by evaporation of the excess epihalohydrin.

The extraction of the catalyst with water is, however, complicated since the organic phase has a greater density than the aqueous phase, thus requiring special equipment, and since emulsions are readily formed which make phase separation difficult. To avoid these emulsions, it is suggested, for example, in German Pat. No. 1,643,777, column 10, either to extract at elevated temperatures or dissolve the epoxy resin in a solvent, e.g. benzene after the alkali halogenide has been filtered off and the excess epichlorohydrin has been distilled off. Although this facilitates the extraction, the epoxy resin solution must be concentrated twice in this process.

It has furthermore been proposed to add aqueous ethanol to prevent the formation of an emulsion of the aqueous phase (Dutch Laid-Open Application No. 6,901,372), but this measure is not effective in the case of several higher-molecular epoxy resins. In the extraction of a 30% solution of a diglycidyl polyester with a molecular mass of 1,000 in epichlorohydrin or in ethyl acetate, the time required for phase separation is reduced from about 24 hours to 4–8 hours when using a 40% aqueous ethanol solution instead of pure water. However, in the usual case of repeated extraction, this time is still too long for a commercial process.

In any event, the removal of the catalyst, required to ensure a sufficient shelf stability of the epoxy resin, is effected in accordance with the state of the art by a repeated extraction with water and/or aqueous solutions, either before or after the separation of the alkali halogenide and before or after the removal of the epihalohydrin or another auxiliary solvent from the reaction mixture obtained during the introduction of the glycidyl groups. These state of the art processes are cumbersome, difficult in part due to poor phase separation, and require large capital expenditures for apparatus to conduct them.

Czechoslovak Pat. No. 119,415 claims a process for refining technical grade epoxy resin by the removal therefrom with adsorbent of trace amounts of residual inorganic salts, water unsoluble macromolecules containing nitrogen and sulfur, which cannot be extracted by water, organic chelates of heavy metals and aluminum and degradation products of the epoxy resin or epichlorohydrin. Since no reference is made to the reaction catalyst and the starting epoxy resin is described as technical grade, it is apparent that the catalyst and the excess epichlorohydrin conventionally employed have been removed from the epoxy resin in a conventional manner, e.g., by washing with water and then placing the washed resin under a vacuum. In any event, from the brief description of the process immediately preceding the examples, it is apparent that prior to the treatment with adsorbent, the epoxy resin has been dissolved in toluene or benzene, freed of water (and apparently also reaction catalyst and excess epichlorohydrin) and the precipitated salts separated by filtration. None of these preliminary steps are required in applicants' process.

It is an object of this invention to provide a process for the removal of the catalyst which avoids the aforedescribed disadvantages of the prior-art processes. Other objects will be apparent to those skilled in the art to which this invention pertains.

SUMMARY OF THE INVENTION

According to the process of this invention, the low molecular water-soluble onium-catalyst dissolved in the liquid mixture of epoxy resin and excess epihalohydrin obtained by the reaction in the presence of base of a compound having —OH, —SH, —COOH or =NH groups with excess 1-halo-2,3-epoxyalkane, is separated therefrom by contacting the liquid mixture, either prior to or after separation therefrom of the precipitated salt produced by the reaction, with at least about 5 parts by weight based on the weight of the catalyst present in the liquid mixture, of an adsorbent containing or capable of absorbing at least 1% by weight of water so strongly that it cannot be removed either by drying over concentrated sulfuric acid or by drying at 110° C. and can only be partially removed by drying at 200° C. under vacuum (about 1 millibar), and then separating the adsorbent with catalyst adsorbed thereon from the liquid mixture.

The stabilized epoxy resin can then be isolated from the liquid mixture by evaporation of the epihalohydrin.

DETAILED DISCUSSION

It is known from German Pat. No. 1,168,907 that adsorbents such as fuller's earth can trigger the polymerization of epoxy compounds. Even if only a minor portion of the epoxy compound in the reaction mixture were polymerized, the possibilities for using the respective epoxy resins would be greatly restricted due to the ensuing marked increase in the viscosity thereof. It was surprising that the catalysts can be removed from concentrated solutions of the epoxy resins in an epihalohydrin by adsorption on the adsorbents of this invention without the occurrence of such disadvantages which would make the process commercially unacceptable.

The structure of the starting epoxy compound is not critical. Numerous examples thereof are disclosed in the German patents and Laid-Open applications cited hereinabove, whose disclosures are incorporated by reference. Preferred are polymerizable epoxy compounds, e.g., those containing more than one epoxy group on an average per molecule, preferably such technically important epoxy compounds containing about two epoxy groups on an average per molecule. Such epoxy compounds are obtained by reacting compounds containing at least two —OH, —SH, —COOH or =NH groups with epihalohydrin. Suitable polyglycidylethers are preferably those which are obtained by etherification of a polyhydric alcohol or phenol with epichlorohydrin employing an alkali agent. Polyhydric alcohols are for example, ethylene glycol, diethylene glycol, triethylene glycol, propylene-1,3-glycol, butane-1,4-diol, pentane-1,5-diol, hexane-1,6-diol, glycerol, 1,1,1-trimethylolpropane, 1,2-dihydroxymethyl-cyclopentane. Preferred are polyhydric phenols as for instance resorcinol, catechol, 1,4-di-hydroxynaphthalene, bis(4-hydroxyphenyl)-methane, bis(4-hydroxyphenyl)-tolylmethane, 4,4'-dihydroxydiphenyl, bis(4-hydroxyphenyl)-sulfone, polyphenols for example as they are especially obtained by reaction of phenol with formaldehyde (so-called novolac epoxy resins) or preferably 2,2-bis(4-hydroxyphenyl)-propane. Examples of polyglycidylethers are butane-1,4-diol diglycidylether, resorcinol diglycidylether, as well as especially diglycidylethers, which are derived from 2,2-bis(4-hydroxymethyl)-propane (bisphenol A) and corresponding to the following average formula

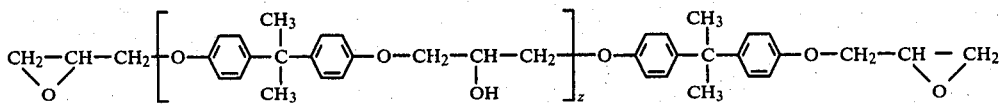

wherein z is a whole or fractional small number, for example between 0 and 2.

Preferred polyglycidylesters are those which are obtained by the reaction of a polycarboxylic acid with epihalohydrin in the presence of an alkali agent. Such polyglycidylesters can be derived from aliphatic dicarboxylic acids, such as succinic acid, adipic acid, sebacic acid, fumaric acid and dimeric linoleic acid, or from aromatic polycarboxylic acids, such as phthalic acid, isophthalic acid, terephthalic acid and trimellitic acid, or from hydroaromatic dicarboxylic acids, such as tetrahydrophthalic acid, hexahydrophthalic acid and 4-methyl-hexahydrophthalic acid. Examples of polyglycidylesters are diglycidyladipate, diglycidylphthalate, diglycidylterephthalate, diglycidyltetrahydrophthalate and diglycidylhexahydrophthalate. Suitable polyglycidylesters are especially those obtained by reaction of a polyesterpolycarboxylic acid with epihalohydrin in the presence of an alkali agent. The number molecular weight of these polyesterpolycarboxylic acids is preferably between 400 and 10,000. The polyesterpolycarboxylic acids are obtained by reactions well known in the art, for example reacting polyhydric alcohols with polycarboxylic acids.

Basic epoxy compounds can also be used. Those compounds are obtained by the reaction of aromatic monoamines, such as aniline, toluidine, or of aromatic secondary diamines, such as 4,4'-di(mono-methylamino)-diphenylmethane, or of cycloaliphatic amines, such as 4,4'-diamino-dicyclohexylmethane, or of heterocyclic compounds containing nitrogen in the ring, such as isocyanuric acid, hydantoin, 5,5-dimethyl-hydantoin, with epihalohydrin in the presence of an alkali agent.

These epoxy compounds are usually prepared from the above-mentioned compounds and epihalohydrin in the presence of an alkali agent and an additional catalyst. The most important catalyst are low-molecular water-soluble quaternary ammonium compounds, quaternary phosphonium compounds and tertiary sulfonium compounds.

Suitable quaternary ammonium compounds are tetramethylammonium chloride, tetramethylammonium hydroxide, tetraethylammonium chloride, tetraethylammonium bromide, methyl-triethylammonium chloride, trimethylbenzylammonium chloride, trimethylbenzylammonium hydroxide, trimethylbenzylammonium acetate, trimethyl-β-hydroxyethylammonium chloride, trimethyl-epoxypropylammonium chloride, trimethyl-hydrazonium iodide. Tertiary amines, which form quaternary ammonium compounds during the glycidilation process, can also be used as catalysts. Examples of such amines are trimethylamine, tri-n-butylamine, dimethylbenzylamine, triethylamine, N,N-dimethylaniline and triethanolamine.

Suitable quaternary phosphonium compounds are tetraphenylphosphonium bromide, tetrabutylphosphonium acetate, benzyl-triphenylphosphonium chloride, methyl-triphenylphosphonium iodide, ethyl-triphenylphosphonium bromide and methyl-tributylphosphonium dimthylphosphate.

Suitable S-containing catalysts are low-molecular thioethers which form sulfonium compounds by reaction with epihalohydrin, for example, diethyl-sulfide, β-hydroxyethylethyl sulfide, β-hydroxypropyl-ethyl sulfide, thiodiglycol, mono-β-cyanoethyl-thioglycol ether, dibenzylsulfide, benzylethyl sulfide and sulfonium compounds such as trimethylsulfonium iodide, tris(hydroxyethyl)-sulfonium chloride, dibenzylmethylsulfonium bromide, dimethyl-benzylsulfonium chloride and 2,3-epoxypropyl-methyl-ethylsulfonium iodide.

Suitable adsorbents include several of the known surface active adsorbents, e.g., clays, such as fuller's earth, kaolinite, bauxite, bentonite, montmorillonite, bleaching clays, and similar substances which also can be chamically treated (activated). Also operable are surface active carbons, as well as silica gels and activated aluminum oxides.

The starting adsorbents must contain or be capable of absorbing at least 1% by weight, e.g., 1–500% by weight, expecially 1–20% by weight of water as swelling and adsorbed water. The adsorbent must be capable of binding at least 1% by weight, especially 4–10% by weight, of water so strongly that it cannot be removed either by drying over concentrated sulfuric acid or by drying at 110° C. and can only be partially removed by drying at 200° C. under vacuum (about 1 mb.). With a content or absorbability of strongly bound water below 1% by weight, the adsorptive effect rapidly decreases. Natural kieselguhr with a surface water content of 0.11% by weight shows hardly any adsorption effect. Likewise ineffective are, for example, polymeric carbohydrates which, although containing a large amount of water in a swollen condition, are readily depleted of this water by drying, as is also the case, for example, of calcium carbonate, basic magnesium carbonate, or French chalk (CaO:MgO). With a water content of between 20 and 500% by weight, part of the water can be transferred to the organic phase, evoking turbidity and thus being possibly undesirable. Preferably, therefore, adsorbents are employed having a water content of between 1 and 20% by weight.

The adsorbents are employed in a quantity of at least 5 parts by weight, based on the parts by weight of catalyst to be removed. If an amount is used which is smaller than this quantity, the removal of the catalyst from the reaction mixture becomes increasingly less efficient within a reasonable time period, or the adsorption time required for the removal of the catalyst is considerably lengthened. The time of treatment with the adsorbent ordinarily is at least about 10 minutes and can be continued for any commercially feasible time usually up to about 2 hours. Under 10 minutes, the adsorption is frequently incomplete and above 2 hours the adsorption is not improved and the danger increases of incurring a polymerization of the epihalohydrin and-/or of the epoxy resins in case of particularly reactive adsorbents.

The temperature during the treatment ordinarily should be about 0°–50° C. with a temperature of 15°–30° C. being preferred. Below 0° C., the adsorption process proceeds markedly more slowly and the fine distribution of the adsorbent becomes more difficult on account of the increased viscosity of the reaction mixture. Above 50° C. no pronounced increase in the adsorption speed occurs and there is the danger, particularly with reactive adsorbents, that a polymerization of the epihalohydrin and/or the epoxy resins will occur. Generally, it is advantageous to effect an immediate fine dispersion when introducing the adsorbents into the reaction mixture to avoid local hot spots above 50° C. It has been found that in this case, even without external cooling, the reaction mixture is not heated up by more than 5° C. during the adsorption process.

When using adsorbents having a low water content, e.g., 1–4% by weight, a water content of the reaction mixture of about 0.05–3% by weight, especially about 1% by weight, frequently provides a better catalyst adsorption, so that a lesser amount of adsorbent is required for the removal of a specific amount of catalyst. In contrast thereto, a water content of above 3% by weight produces no further improvement. In fact, the subsequent separation of the solids, especially the salt, from the reaction mixture is more difficult.

The liquid reaction mixture can be treated so that the adsorbent is distributed in the liquid reaction mixture and is separated from the latter after the desired adsorption time has elapsed. However, it is also possible to pass the reaction mixture through a column or bed charged with the adsorbent at a rate such that the necessary treatment times are maintained.

The salt present in the reaction mixture can be separated before the treatment with the adsorbent. Preferably, however, the salt is removed simultaneously with the catalyst-containing adsorbent, e.g., by filtration or centrifugation, since in such a case the entire work-up procedure for the reaction mixture involves merely a single solids separation and then concentration of the thus-obtained solution of purified epoxy resin.

Although the sole solvent for starting epoxy resin ordinarily is the excess unreacted epihalohydrin, e.g., epichlorohydrin or β-methylepichlorohydrin, it will be apparent that an obvious equivalent is the removal of the catalyst from liquid reaction mixtures containing an additional solvent, such as, for example, ethyl acetate or methylene chloride, since the additional solvent can be removed by volatilization concurrently with the epichlorohydrin. However, such additional solvent is unnecessary and complicates the recovery of the excess epihalohydrin for re-use.

The excess epihalohydrin can then be removed conventionally by evaporation, after the separation of the salt and the catalyst-containing adsorbent. If the salt is separated before the treatment with adsorbent, any residual salt is removed from the epoxy resin along with the catalyst-containing adsorbent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The adsorptions are conducted with reaction mixtures obtained by the glycidylation of various compounds. Percentages are weight percent. Unless indicated otherwise, the sodium chloride was separated before the adsorption experiments. The reaction mixtures, also called "mixtures" in the following examples, all contained between 0.05 and 0.5% of water.

The starting mixtures employed in the process of this invention are described below:

MIXTURE A

This liquid reaction mixture consisted of a 30% solution in epichlorohydrin of a diglycidyl ester (molar mass about 1,000), obtained in the conventional manner by the glycidylation, in the presence of 12.0 g. tetraethylammonium bromide (TEAB) employed as the catalyst, with 2550 g. of epichlorohydrin of 800 g. of polyester-dicarboxylic acid produced from the ethylene glycol and phthalic anhydride in a molar ratio of 3:4.

The amount of the catalyst in the liquid reaction mixture was determined as follows: Solvent-free epoxy resin was obtained by concentration of an aliquot sample of the liquid reaction mixture under vacuum. From its nitrogen content of 0.076% N, a catalyst content of $\triangleq$ 1.14% by weight was determined by calculation.

MIXTURE B

This was the same reaction mixture as Mixture A, except the catalyst content of the diglycidyl ester, as determined by concentration of an aliquot under vacuum, was 0.18% by weight of TEAB. (The glycidylation was conducted wth the same amounts of polyester-dicarboxylic acid and epichlorohydrin as in Mixture A, but with 2.0 g TEAB).

MIXTURE C

This liquid reaction mixture consisted of a 46% solution in epichlorohydrin of a diglycidyl ester prepared by the reaction, in the presence of 19.5 g. of tetramethylammonium chloride (TMAC) as the catalyst, of 1850 g. of epichlorohydrin and 600 g. of a polyester-dicarboxylic acid (molar mass about 600) obtained by reacting 1,6-hexanediol and adipic acid in a molar ratio of 2:3.

The crude epoxy resin, obtainable by direct concentration of an aliquot of the liquid reaction mixture, had a catalyst content of 2.60%.

MIXTURE D

This liquid reaction mixture consisted of a 27% solution in epichlorohydrin of the same glycidyl ester as in Mixture C, except the concentrated crude epoxy resin contained 0.23% of TMAC. (The glycidylation was conducted as in mixture C with the same amounts of polyester-dicarboxylic acid and epichlorhydrin, but with 1.75 g TMAC).

MIXTURE E

This liquid reaction mixture consisted of a 30% solution in epichlorohydrin of an epoxy resin consisting essentially of bisphenol A bis-blycidyl ether (molar mass about 380), and containing the TEAB as the catalyst. The resin was produced by reacting 228 g bisphenol A with 1400 g epichlorohydrin in the presence of 3.9 g TEAB as the catalyst and adding 2.2 moles of 50% aqueous NaOH-solution.

A sample of the crude diglycidyl ether obtained by direct concentration of an aliquot of the reaction mixture contained 1.02% of TEAB.

The catalyst was removed from the above mixtures in accordance with the following methods:

METHOD Y (DISCONTINUOUS)

Using one of the aforedescribed mixtures, the adsorbent was added thereto under agitation at room temperature. The mixture was then agitated for another 10–120 minutes. After separating the adsorbent, the epichlorohydrin was evaporated under vacuum at 80° C. until constant weight was attained. (This concentrating step is unnecessary with mixtures which are free of epichlorohydrin and solvents.) The nitrogen content of the residual epoxy resin was determined (method according to Kjelldahl, detection limit 0.001 % N) and the corresponding catalyst content was calculated therefrom.

METHOD Z (CONTINUOUS)

One of the above-described mixtures was passed through a column filled with the adsorbent with a residence time of about 10–60 minutes. The internal diameter of the column was 2 cm.

The results of the adsorption tests (Examples 1–24) are compiled in the following table. The reduction in nitrogen content characterizes the effectiveness of the respective adsorbent in removing the catalyst.

| Example No. | Mixture | Adsorbent (Manufacturer) | Amount of Adsorbent % (1) | Method | Catalyst Content (% by Weight) (1) Before Adsorp. | After Adsorp. |
|---|---|---|---|---|---|---|
| 1 | A | Silica gel, 0.2–0.5 mm. (Woelm) | 30 | Y | 1.14 | 0.045 |
| 2 | A | Silica gel, 0.2–0.5 mm. (Woelm) + 1% H$_2$O (2) | 30 | Y | 1.14 | 0.03 |
| 3 | A | Silica gel, 0.2–0.5 mm. (Woelm) | 100 | Z | 1.14 | 0.03 |
| 4 | A | Silica gel (Herrmann, Koeln), 3–4 mm. | 100 | Z | 1.14 | 0.03 |
| 5 | A | Silica gel (Herrmann, Koeln), 0.3–0.75 mm. | 60 | Z | 1.14 | 0.015 |
| 6 | A | Al$_2$O$_3$ acc. to Brockmann, A-stage I, acidic | 40 | Y | 1.14 | 0.3 |
| 7 | A | Al$_2$O$_3$ acc. to Brockmann, A-stage I, basic | 40 | Y | 1.14 | 0.225 |
| 8 | A | Al$_2$O$_3$ acc. to Brockmann, A-stage I, neutral | 30 | Y | 1.14 | 0.465 |
| 9 | A | Al$_2$O$_3$ acc. to Brockmann, A-stage III, neutral | 30 | Y | 1.14 | 0.21 |
| 10 | A | Al$_2$O$_3$ acc. to Brockmann, | 60 | Y | 1.14 | 0.03 |

-continued

| No. | | Adsorbent | | | | |
|---|---|---|---|---|---|---|
| 11 | A | A-stage I, basic Decolorizing carbon, water content 6% ("Carboraffin," Bayer) | 30 | Y | 1.14 | 0.12 |
| 12 | A | Silica gel, 0.2–0.5 mm. (Woelm) | 7.5 | Y | 1.14 | 0.045 |
| 13 | A | Bolus alba, DAB 6 [German Pharmacopeia] (Riedel-de-Haen) | 30 | Y | 1.14 | 0.105 |
| 14 | A | Bleaching clay (3), water content 10% (4) (E. Merck, Darmstadt) | 7.5 | Y | 1.14 | 0.045 |
| 15 | A | Diatomaceous earth ("Celite" 512, Johns Manville Products Co.) | 30 | Y | 1.14 | 0.105 |
| 16 | B | Silica gel (Herrmann, Koeln) 0.3–0.75 mm. | 60 | Z | 0.18 | 0.015 |
| 17 | B | Bolus alba, DAB 6 (Riedel-de-Haen) | 7.5 | Y | 0.18 | 0.015 |
| 18 | B | Bleaching clay (3), water content 10% (4) (E. Merck, Darmstadt) | 3.75 | Y | 0.18 | 0.045 |
| 19 | B | Decolorizing carbon, water content 6% ("Carboraffin" Bayer) | 3.75 | Y | 0.18 | 0.045 |
| 20 | B | Diatomaceous earth ("Celite" 512, Johns Manville Products Co.) | 15 | Y | 0.18 | 0.015 |
| 21 | B | $Al_2O_3$ acc. to Brockmann, A-stage I, basic | 60 | Z | 0.18 | 0.015 |
| 22 | C | Silica gel (Herrmann, Koeln) 0.3–0.75 mm. | 30 | Z | 2.60 | 0.396 |
| 23 | D | Silica gel (Herrmann, Koeln) 0.3–0.75 mm. | 40 | Z | 0.23 | 0.015 |
| 24 | E | Silica gel, 0.2–0.5 mm. (Woelm) | 200 | Z | 1.02 | 0.06 |
| 25 | E | Bleaching day (3), water content 10% (4) (E. Merck, Darmstadt) | 10 | Y | 1.02 | 0.075 |

(1) Based on the epoxy resin in the mixture.
(2) Based on the reaction mixture; the water was added to the mixture before the beginning of the adsorption.
(3) When using highly active adsorbents, such as bleaching clay, fuller's earth, or "Tonsil", a polymerization can occur in certain cases at higher temperatures by way of oxirane groups. Therefore, it is advantageous to ensure good and rapid dispersion of the adsorbent, to avoid local hot spots occurring due to the heat of adsorption, resulting possibly in loss of material due to polymerization.
(4) Water contents of commercial adsorbents, determined by the drying loss at 200° C. and 0.1 mb.:

| | |
|---|---|
| Bleaching clay | 10% |
| "Tonsil" AC | 7% |
| Decolorizing carbon | 6% |
| Silica gel (Woelm) | 10% |
| Silica gel (Herrmann, Koeln) | 8.5% |
| $Al_2O_3$ to Brockmann A-stage I | 1% |
| $Al_2O_3$ to Brockmann, A-stage III | 7% |
| Bolus alba, DAB6 [German Pharmacopeia] (Riedel de-Haen) | 14% |
| Diatomaceous earth ("Celite") 512, Johns Manville Products Co.) | 1% |

Other water contents were produced by partial drying and/or by adding water to the adsorbent and/or to the reaction mixture.

EXAMPLE 26 (Commercial Scale)

By the glycidylation, in the presence of 150 g. of TEAB as catalyst, with 170 kg. epichlorohydrin of 31 kg. of a polyester-dicarboxylic acid (MW≈450), produced from trimethylolpropane and hexahydrophthalic anhydride in a molar ratio of 1:2, a liquid reaction mixture was obtained consisting essentially of 40 kg. of bis-glycidyl ester, 150 kg. of epichlorohydrin, 15 kg. of sodium chloride, and 150 g. of TEAB, corresponding to a 0.375% catalyst content based on the bisglycidyl ester. Under vigorous agitation, 4 kg. of bleaching clay (water content 10%, E. Merck, Darmstadt, Germany) was introduced and the mixture further stirred for 30 minutes. After filtration of the solids and concentration of the solution, clear bis-glycidyl ester was obtained, having a nitrogen content of 0.002%, which corresponds to 0.03% of TEAB catalyst content.

EXAMPLE 27

The starting liquid reaction mixture consisted of a 50% solution of a diglycidyl ester (molecular mass about 550) in epichlorohydrin, obtained by glycidylation with 800 g. of epichlorohydrin of a 370 g. polyester-dicarboxylic acid, prepared from ethylene glycol and hexahydrophthalic anhydride in a molar ratio of 1:2, in the presence of 10.5 g. tetraphenylphosphonium bromide as the catalyst.

The crude epoxy resin, obtainable by direct concentration of an aliquot of the liquid reaction mixture, had a content of 1.89% of tetraphenylphosphonium bromide (calculated by the analytically determined P-content).

To 200 g. of this liquid reaction mixture was added 20 g. of bleaching clay (E. Merck, Darmstadt; water content 10%) under agitation at ambient temperature (30 minutes). After separating the adsorbent, the epichlorohydrin was evaporated under vacuum at 80° C. until constant weight was attained. The residual epoxy resin had a catalyst content of 0.13% of tetraphenylphosphonium bromide. The same result was obtained employing 20 g. of montmorillonite (Tonsil® AC, Suedchemie, water content 7%).

EXAMPLE 28

The reaction mixture consisted of a 50% solution of a diglycidyl ester (molecular mass about 570) in epichlorohydrin, obtained by glycidylation with 370 g. of the same polyesterdicarboxylic acid as in Example 27, with 800 g. of epichlorohydrin in the presence of 3,5 g. dimethyl-benzylsulfonium chloride as catalyst. The crude epoxy resin obtained by direct concentration of an aliquot of the reaction mixture had a 0.65% content of dimethyl-benzylsulfonium chloride (calculated by the analytically determined S-content).

After treating 200 g. of the reaction mixture with 15 g. of bleaching clay (E. Merck, Darmstadt; water content 10%), following the procedure described in Example 27, a purified epoxy resin having a 0.084% content of dimethyl-benzylsulfonium chloride was obtained.

The preceding examples can be repeated with similar sucess by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the separation of the low molecular water-soluble onium-catalyst dissolved in the liquid mixture of epoxy resin and epihalohydrin obtained by the reaction in the presence of base of a compound having —OH, —SH, —COOH or =NH groups with excess 1-halo-2,3-epoxyalkane, consisting essentially of contacting the liquid mixture, either prior to or after separation therefrom of the precipitated salt produced by the reaction, with at least about 5 parts by weight based on the weight of the catalyst present in the liquid mixture, of an adsorbent containing or capable of absorbing at least 1% by weight of water so strongly that it cannot be removed either by drying over concentrated sulfuric acid or by drying at 110° C. and can only be partially removed by drying at 200° C. under vacuum (about 1 millibar), and then separating the adsorbent with catalyst adsorbed thereon from the liquid mixture.

2. A process according to claim 1, wherein the adsorbent is activated carbon, bleaching clay, fuller's earth, bauxite, bentonite, kaolinite, montmorillonite, kieselguhr, silica gel, or aluminum oxide.

3. A process according to claim 1, wherein the adsorbent has a water content of 1–4% by weight.

4. A process according to claim 1, wherein the starting liquid reaction mixture contains 0.05–3% by weight of water.

5. A process according to claim 1, wherein the catalyst is a water-soluble ammonium-, phosphonium- or sulfonium compound.

6. A process according to claim 1, wherein the 1-halo-2,3-epoxyalkane is epichlorohydrin or β-methylepichlorohydrin.

7. A process according to claim 6, wherein the adsorbent is mixed with a starting liquid mixture containing suspended therein the sodium chloride produced in the production of the epoxy resin.

8. A process according to claim 1, wherein the process is conducted batch-wise by adding the adsorbent to the starting liquid reaction mixture.

9. A process according to claim 1, wherein the process is conducted continuously by passing the starting liquid reaction mixture through a column of the adsorbent.

10. A process according to claim 1 wherein the 1-halo-2,3-epoxyalkane is epichlorohydrin or β-methylepichlorohydrin, wherein the adsorbent is mixed at ambient temperature with a starting liquid mixture containing suspended therein the sodium chloride produced in the production of the epoxy resin, and wherein the process is conducted batch-wise by adding the adsorbent to the starting liquid reaction mixture.

* * * * *